United States Patent
Shen et al.

(10) Patent No.: US 9,373,181 B2
(45) Date of Patent: Jun. 21, 2016

(54) SYSTEM AND METHOD FOR ENHANCED VIEWING OF RIB METASTASIS

(75) Inventors: Hong Shen, Plainsboro, NJ (US); Shuping Qing, Princeton, NJ (US)

(73) Assignee: Siemens Medical Soultions USA, Inc., Malvern, PA (US)

( * ) Notice: Subject to any disclaimer, the term of this patent is extended or adjusted under 35 U.S.C. 154(b) by 1732 days.

(21) Appl. No.: 11/539,377

(22) Filed: Oct. 6, 2006

(65) Prior Publication Data

US 2007/0110295 A1    May 17, 2007

Related U.S. Application Data

(60) Provisional application No. 60/727,573, filed on Oct. 17, 2005.

(51) Int. Cl.
| | |
|---|---|
| G06K 9/00 | (2006.01) |
| G06T 11/00 | (2006.01) |
| G06T 7/00 | (2006.01) |
| G06T 19/00 | (2011.01) |
| A61B 6/03 | (2006.01) |

(52) U.S. Cl.
CPC .............. G06T 11/008 (2013.01); G06T 7/0012 (2013.01); G06T 19/00 (2013.01); A61B 6/03 (2013.01); G06T 2207/10081 (2013.01); G06T 2207/20161 (2013.01); G06T 2207/30008 (2013.01); G06T 2207/30096 (2013.01)

(58) Field of Classification Search
CPC ........... G06T 2207/30004; G06T 2207/10081; G06T 2207/30008; A61B 6/03; A61B 6/037; A61B 6/481; A61B 6/505
USPC ........................... 382/294, 128–132; 600/437
See application file for complete search history.

(56) References Cited

U.S. PATENT DOCUMENTS

| | | | |
|---|---|---|---|
| 6,266,453 B1 * | 7/2001 | Hibbard et al. ............... | 382/294 |
| 6,577,752 B2 * | 6/2003 | Armato, III .......... | G06T 7/0012 |
| | | | 382/131 |
| 2003/0026390 A1 * | 2/2003 | Lutz .............................. | 378/210 |
| 2003/0212327 A1 * | 11/2003 | Wang et al. ................... | 600/437 |
| 2004/0062786 A1 * | 4/2004 | Ascenzi et al. ............... | 424/423 |
| 2005/0010107 A1 | 1/2005 | Shen | |
| 2005/0265606 A1 * | 12/2005 | Nakamura .................... | 382/218 |
| 2006/0047195 A1 * | 3/2006 | Shen ..................... | G06F 19/345 |
| | | | 600/407 |
| 2006/0062425 A1 | 3/2006 | Shen et al. | |
| 2006/0173271 A1 | 8/2006 | Shen et al. | |
| 2006/0173272 A1 | 8/2006 | Qing et al. | |

OTHER PUBLICATIONS

Hong et al. ("Tracing Based Segmentation for the labeling if Individual Rib Structures in Chest CT Volume Data", MICCAI 2004, LNCS 3217, pp. 967-974, 2004).*

(Continued)

*Primary Examiner* — Amara Abdi

(57) ABSTRACT

A system and method for enhanced viewing of rib metastasis in CT volume data is disclosed. The system and method receive input CT volume data and display slices of the CT volume data. Ribs are automatically segmented from the CT volume data, ordered and labeled. A 3D visualization of the ribs is generated and displayed. Alterations in the rib structure is automatically detected using shape based analysis of the ribs. The alterations are marked as candidate locations for rib metastasis in the displayed slices and 3D visualization in order to assist in the diagnosis of rib metastasis.

22 Claims, 5 Drawing Sheets

(56) References Cited

OTHER PUBLICATIONS

Dehmeshki et al. ("Shape based region growing using derivatives of 3D medical images: Application to semi-automated detection of pulmonary nodules", London, WIJ 5AT, UK, 2003 IEEE).*

Dehmeshki et al. ("Shape Based Region Growing using derivatives of 3D Medical Images: Application to Automatic detection of pulmonary Nodules" Proceedings of the 3D international symposium if image signal processing and analysis, IEEE 2003).*

Dehmeshki ("Shape Based Region Growing using derivatives of 3D Medical Images: Application to Automatic detection of pulmonary Nodules" Proceedings of the 3D international symposium if image signal processing and analysis, IEEE 2003).*

* cited by examiner

SYSTEM AND METHOD FOR ENHANCED VIEWING OF RIB METASTASIS

This application claims the benefit of U.S. Provisional Application No. 60/727,573 filed Oct. 17, 2005, the disclosure of which is herein incorporated by reference.

BACKGROUND OF THE INVENTION

The present invention relates to viewing ribs in computed tomography (CT) volume data, and more particularly to a system and method for enhanced viewing of rib metastasis using CT volume data.

Computed tomography (CT) is a medical imaging method whereby digital geometry processing is used to generate a three-dimensional image of the internal features of a patient from a large series of two-dimensional X-ray images taken around a single axis of rotation. Such CT imaging results in CT volume data which is a virtual representation of internal anatomical features of a patient. The CT volume data consists of multiple slices, or two-dimensional images, that can be combined to generate a three dimensional image. CT imaging is particularly useful because it can show several types of tissue including lung, bone, soft tissue and blood vessels, with great clarity. Accordingly, such imaging of the body can be used to diagnose problems such as cancers, cardiovascular disease, infectious disease, trauma and musculoskeletal disorders.

CT imaging is commonly used to diagnose rib metastasis. Metastasis is the spread of cancer from its primary site to other places in the body. Rib metastasis is caused by cancerous cells from a primary tumor relocating to the ribs. Approximately 170,000 new cases of bone metastases are diagnosed annually in the United States. Over 500,000 Americans live with bone metastases. Primary carcinomas that frequently metastasize to bone include those from breast, lung, prostate, kidney, thyroid, stomach, and intestinal cancer.

In order to diagnose rib metastasis, a doctor typically searched for rib metastases in chest CT images generated from a CT volume data. A typical CT volume data set can contain hundreds of slices. FIG. 1 illustrates an exemplary axial slice 100 of a chest CT volume data set. The axial slice 100 is a view generated along an axial plane, which is orthogonal to the long axis of the body. As illustrated in FIG. 1, multiple ellipsoid shaped bright areas 102, 104, 106, 108, 110, and 112 can be seen in the axial slice 100. These ellipsoid shaped bright areas, 102, 104, 106, 108, 110, and 112 are the intersections of ribs with the axial plane. In order to diagnose rib metastasis, a doctor must typically look at hundreds of such slices and on each slice study each of the rib intersections to look for possible metastasis. This diagnosis process is very tedious and error prone.

Once a possible metastasis is discovered on a rib, the doctor needs to identify which rib it is. However, there are no specific features which differentiate ribs from one another. Furthermore, ribs typically cross through the axial planes at an oblique angle making their identification problematic. Accordingly, accurately identify a particular rib is typically a long and difficult process.

BRIEF SUMMARY OF THE INVENTION

The present invention is directed to a system and method for assisting in the diagnosis of rib metastasis. The interface and method of the present invention are capable of automatically locating alterations in rib structure. The interface and method of the present invention are also capable of automatically labeling individual ribs.

In one embodiment of the present invention, a method for enhanced viewing of rib metastasis can be performed by a processor of a computer system. This method may be defined by computer program instructions on a computer readable medium. In this embodiment, computed tomography (CT) volume data is received, ribs in the CT volume data are automatically labeled, and alterations in a structure of the ribs are automatically detected. The ribs are automatically labeled by segmenting the ribs from the CT volume data, ordering the ribs based on relative sizes and shapes of the ribs, and assigning a label, such as a rib number, to each ordered rib. Slices of the CT volume data as well as a 3D visualization of the ribs can be displayed. The alterations are detected using shape based analysis of the ribs, and the detected alterations are marked on the displayed slices and 3D visualization.

In another embodiment of the present invention, an interface for enhanced viewing of rib metastasis includes at least one main window and a 3D window. The main window displays slices of CT volume data and the 3D window displays a 3D visualization of ribs extracted from the CT volume data. The interface also includes a rib label field which indicates a rib number of a rib displayed in the main window or the 3D window, as well as markers indicating locations of detected alterations to the rib structure on the displayed slices and 3D visualization. The main window and 3D window are spatially correlated such that the image displayed on one of the windows is adjusted based on user input to the other window.

These and other advantages of the invention will be apparent to those of ordinary skill in the art by reference to the following detailed description and the accompanying drawings.

DETAILED DESCRIPTION OF EXEMPLARY EMBODIMENTS

Figure 1:
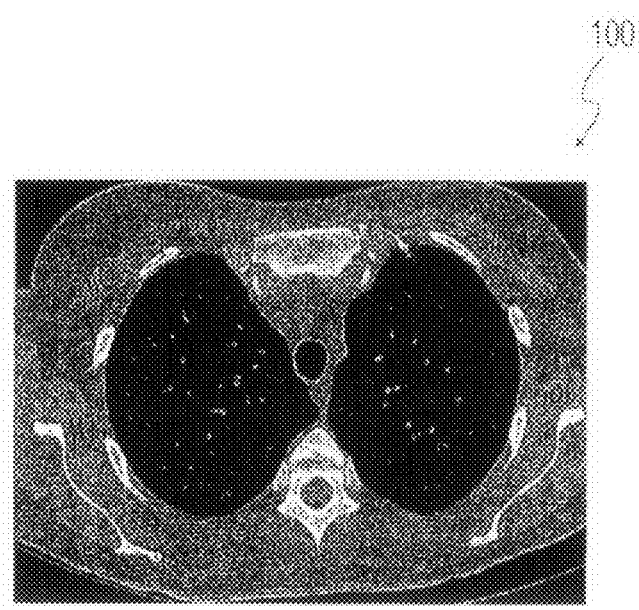
FIG. 1 illustrates an exemplary axial slice of a chest CT volume data set.
Figure 2:
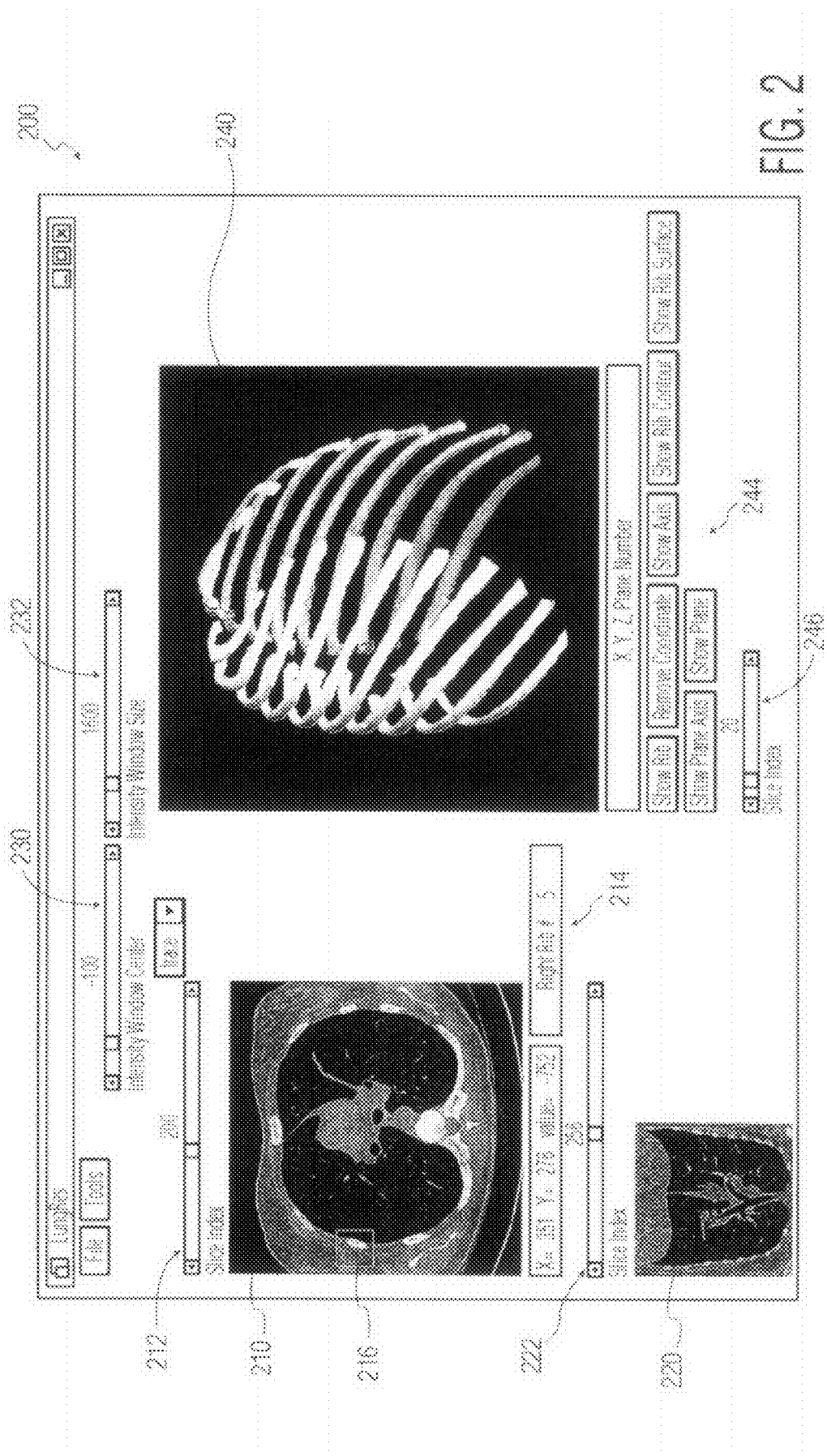
FIG. 2 illustrates a system interface for enhanced viewing of rib metastasis according to an embodiment of the present invention.
Figure 3:
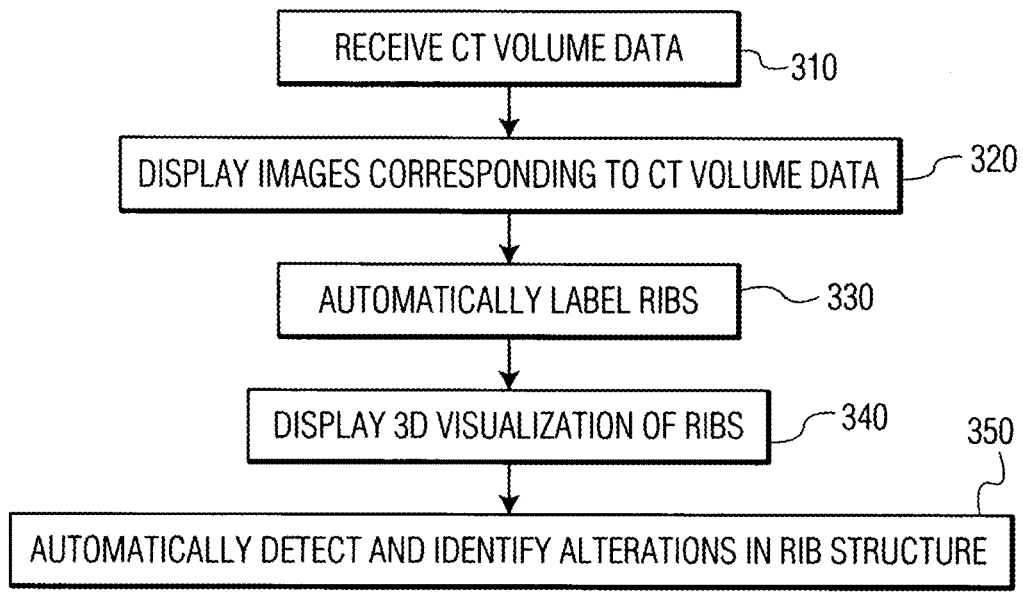
FIG. 3 illustrates a method for enhanced viewing of rib metastasis according to an embodiment of the present invention.

FIG. 2 illustrates a system interface 200 for the enhanced viewing of rib metastasis according to an embodiment of the present invention. The system interface 200 is displayed by a display portion of a computer system and controlled by a processor of the computer system, which is adapted to execute computer program instructions. FIG. 3 illustrates a method for enhanced viewing of rib metastasis according to an embodiment of the present invention. This method is performed by a rib metastasis visualization system running on a computer system. This method is described while referring to FIGS. 2 and 3.

At step 310, CT volume data is received. The CT volume data can be CT volume data resulting from a chest CT scan. This CT volume data can be stored in memory of a computer system and loaded to a rib metastasis visualization system running on the computer system (or another computer system). The CT volume data may be stored and loaded in a standard image format. For example, the CT volume data can be stored and loaded using the DICOM (Digital Imaging and Communications in Medicine) standard, which is a commonly used standard for the transfer and storage of medical images. It is possible that multiple sets of CT volume data are input for simultaneous visualization.

At step 320, images corresponding to the CT volume data are displayed on the system interface 200. The system interface 200 can display slices of the CT volume data on one or more main windows 210 and 220. As illustrated in FIG. 2, the system interface includes an axial main window 210 and a sagittal main window 220 for displaying axial and sagittal slices of the CT volume data, respectively. An axial slice is a view generated along an axial plane, which is orthogonal to the long axis of the body, whereas a sagittal slice is a view generated along a sagittal plane which is parallel to the long axis of the body and divides the body into left and right portions. The main windows 210 and 220 are each associated with a slice index 212 and 222, respectively. Each slice index 212 and 222 control which slice is displayed in the associated main window 210 and 220, and indicate which slice is currently being displayed in the associated main window 210 and 220.

In order to display the slices of the CT volume data in the main windows 210 and 220, a windowing operation is performed on the CT volume data. The CT volume data is typically generated and stored as 10-bit data, where each pixel has an intensity value in the range 0-1024. Windowing is an operation that selects an 8-bit portion of the 10-bit intensity values to be displayed on an 8-bit display. The 8-bit intensity values correspond to shades of grey running from black (0) to white (255). In a windowing operation, any 10-bit intensity value less than the smallest value in an intensity window is mapped to 0, and any intensity value greater than the largest intensity value in the intensity window is mapped to 255. The center of the intensity window and the size of the intensity window can be selected and adjusted by a user. As illustrated in FIG. 2, the system interface 200 includes an intensity widow center selection bar 230 and an intensity window size selection bar 232 for selecting and adjusting the center and the size of the intensity window, respectively. It is also possible that the windowing settings (center and size of the intensity window) be automatically determined by the rib metastasis visualization system. The automatically detected windowing settings can be adjusted by a user using the selection bars 230 and 232. The system can also store default windowing settings and preferred windowing settings of specific users.

Figure 4:
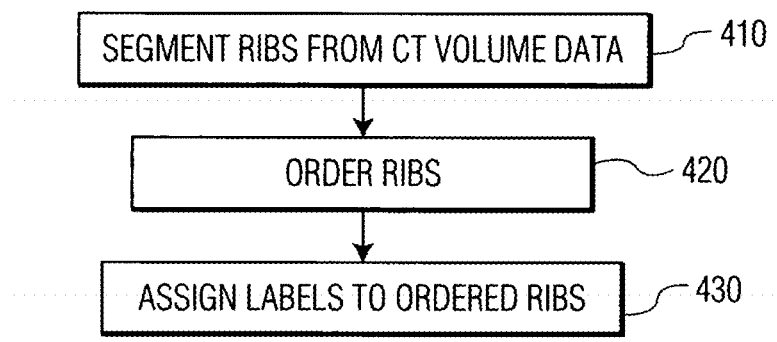
FIG. 4 illustrates a method for labeling ribs in CT volume data according to an embodiment of the present invention.

At step 330, ribs in the CT volume data are automatically labeled. This step is described in greater detail in FIG. 4, which illustrates a method for labeling ribs in CT volume data according to an embodiment of the present invention. This method can be performed internally in a computer system running the rib metastasis visualization system. Referring to FIG. 4, at step 410, ribs are segmented from the CT volume data. As used herein, segmenting ribs from CT volume data refers to extracting data representing individual ribs from the CT volume data. For example co-pending U.S. patent application Ser. No. 11/203,792 discloses a fast tracing based technique to extract the ribs from the CT volume data. This technique may be used to extract the ribs, resulting in separate data representing each rib.

At step 420, the extracted (segmented) ribs are ordered based on a size and shape of each rib. More particularly relative spatial relationships and length ratios of each of the ribs are compared in order to determine an order of the ribs. Although no specific features typically exist on the ribs to distinguish one rib from another, the ribs can be distinguished based on relative size and shape with respect to each other. From the relative locations of seed points for each rib, the relative spatial orders of the ribs from top to bottom and from left and right can be estimated. Further, the symmetrical axis of the thoracic cage is computed from all the extracted centerline points of the ribs. The ribs are then grouped into pairs according to their locations in the direction of the symmetrical axis. After ordering and grouping, the counting of ribs starts from the top of the thoracic cage and goes to the bottom. This becomes more complex when the data only contains part of the thoracic cage. The topmost ribs can be identified based on the fact that from the top to the bottom, the areas enclosed by a pair of ribs increases and the shape of a regions enclosed by a pair of ribs varies. The areas and lengths ratios are used as features to identify the top most rib. Once the numbers of topmost ribs in the data set are identified, the remaining ribs are counter and numbered from the topmost ribs.

At step 430, labels are assigned to the ordered ribs. In medical practice, each rib is assigned a unique label including the side of the body of the rib and the rib number (assigned from top to bottom on each side) of the rib. For example, the fifth rib from the top on the right side of the body can be assigned the label, "Right rib #5". The labels are used to identify the ribs in the system interface 200. When a user clicks on a rib using a mouse or the like (or simply hold a pointer over a rib), the system interfaces 200 automatically displays the rib number of that rib. For example, as illustrated in FIG. 2, a rib label field 214 indicates that "Right rib #5" has been selected in the axial main window 210.

Returning to FIG. 3, at step 340, a 3D visualization of ribs is displayed. The tracing based algorithm used to segment the ribs extracts the centerline and sample boundary points on the ribs. The boundaries of the ribs are obtained by connecting the boundary points. Therefore, the boundaries of the ribs may not be accurate. Once the data corresponding to the individual ribs is segmented and ordered, the segmented ribs can be refined using a level set method to obtain the more accurate boundaries. For example, co-pending U.S. patent application Ser. No. 11/334,278 discloses such a level set method for refinement of rib segmentation in chest CT volume data. A 3D image of the segmented ribs is then generated and displayed. As illustrated in FIG. 2, the system interface 200 includes a 3D window 240 for displaying the 3D visualization of the ribs. The 3D window is spatially correlated with the main windows 210 and 220. Accordingly, the 3D visualization of the ribs can be used to give an overview of the rib structure in the CT volume data as well as to navigate the CT volume data. For example, when a user selects a rib in the 3D window 240, a corresponding axial slice showing that rib is automatically displayed in the axial main window 210. Similarly, when a user selects a rib in the axial main window 210, the 3D visualization displayed in the 3D window 240 can be automatically rotated and/or zoomed to focus on that rib or a 3D visualization of the individual rib can be displayed in the 3D window 240. As illustrated in FIG. 2, in response to a click on a rib in the 3D window 240 at point 242, the main axial window 210 displays a corresponding slice with a marking box 216 indicating a location corresponding to point 242. The system interface 200 provides rotating and zooming functions, as well as other functions to enhance viewing of the 3D visualization. The system interface 200 includes control buttons 244 for controlling these functions. In addition to a 3D visualization of all of the ribs, as illustrated in FIG. 2, the 3D window 240 is also capable of displaying a 3D visualization of one or more individual ribs. The 3D window is associated with a slice index 246 for controlling which slice displayed in the 3D window 240 and indicating which slice is currently being displayed in the 3D window 240.

Figure 5:
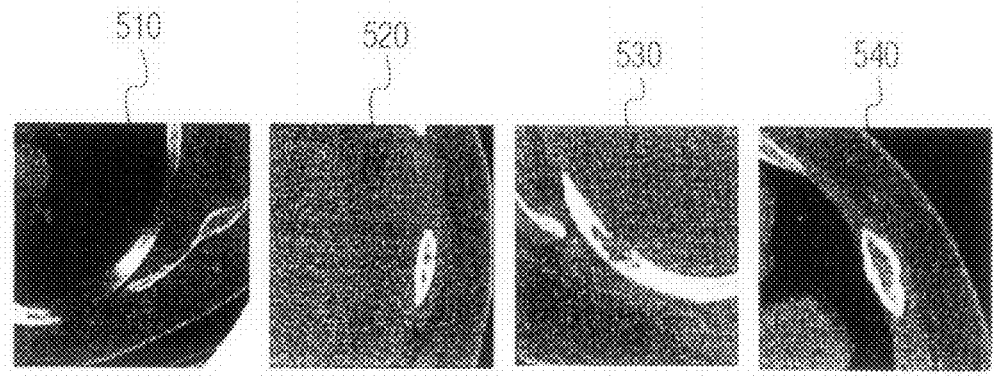
FIG. 5 illustrates exemplary alterations of rib structure due to rib metastasis.
Figure 6:
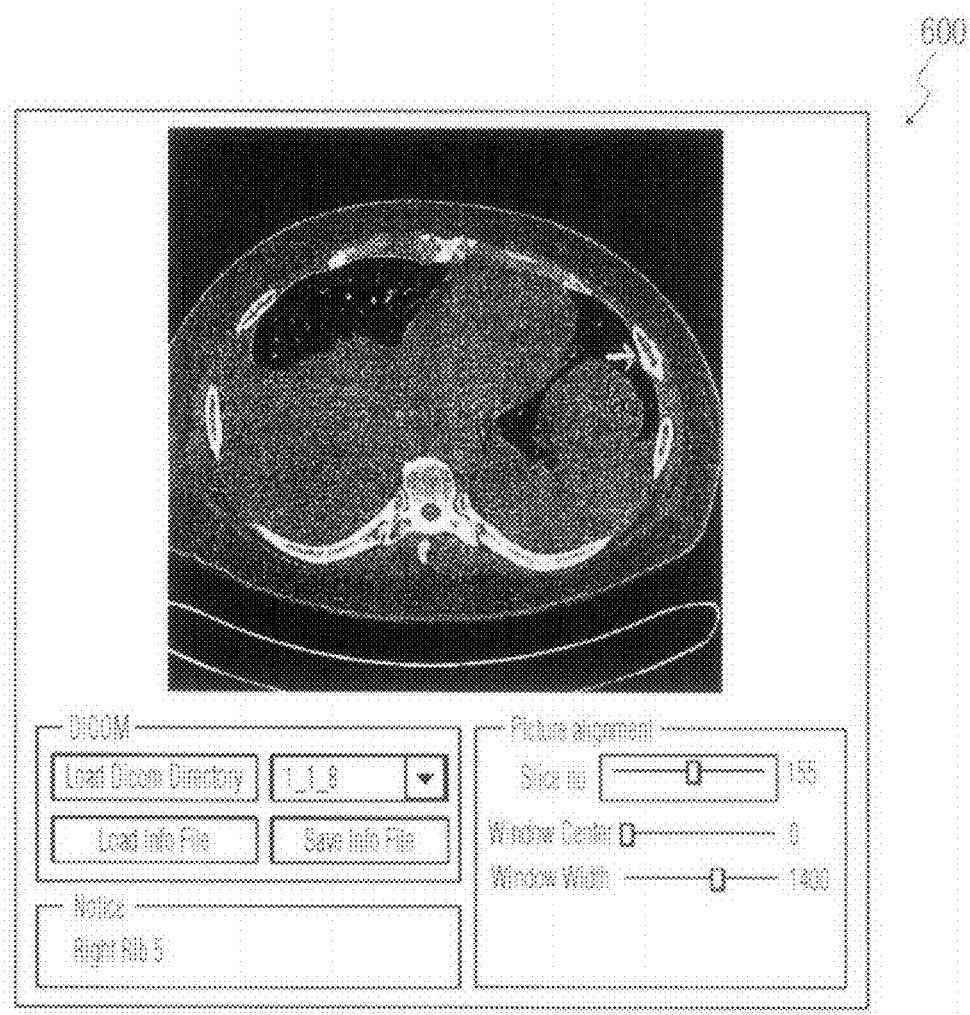
FIG. 6 illustrates an exemplary axial slice which is marked to identify a candidate location where an alteration is detected.

At step 350, alterations in the rib structure are automatically detected and identified. An alteration is any abnormality in the rib structure. Any alteration identified in the rib structure is a candidate for rib metastasis. FIG. 5 illustrates images 510, 520, 530, and 540 showing exemplary alterations of rib structure due to rib metastasis. As illustrated in FIG. 5, these alterations can include intensity changes in the trabecular bone or cortical bone, as well as altered or broken boundaries. For example, images 510 and 520 illustrate an increase in trabecular bone density, image 530 illustrates a rib structure having broken boundaries, and image 540 illustrates enlargement of the bone of a rib. In order to detect these alterations shaped based analysis is performed on each of the ribs to detect abnormalities. Candidate locations (i.e., locations of detected alterations) are generated by the shape based analysis, and then filtered using a set of image analysis procedures. For example, shape and intensity features representing the alterations can be extracted and rules can be applied to these features to determine which type of alterations are identified. The candidate locations are then marked on the images displayed by the system interface 200. FIG. 6 illustrates an exemplary axial slice 600 which is marked to identify a candidate location where an alteration is detected. As illustrated in FIG. 6, the axial slice 600 is marked with an arrow 602 to indicate the candidate location. The axial slice 600 of FIG. 6 corresponds to an image displayed by the axial main window 210 of the system interface 200 of FIG. 2. Similarly, candidate locations can be marked in the 3D visualization of the ribs displayed in the 3D window 240. The marked candidate locations are easily visible to a user when navigating the CT volume data on the system interface 200. Accordingly, the method and system interface 200 assists users in diagnosing rib metastasis by identifying likely candidate locations for rib metastasis.

Figure 7:
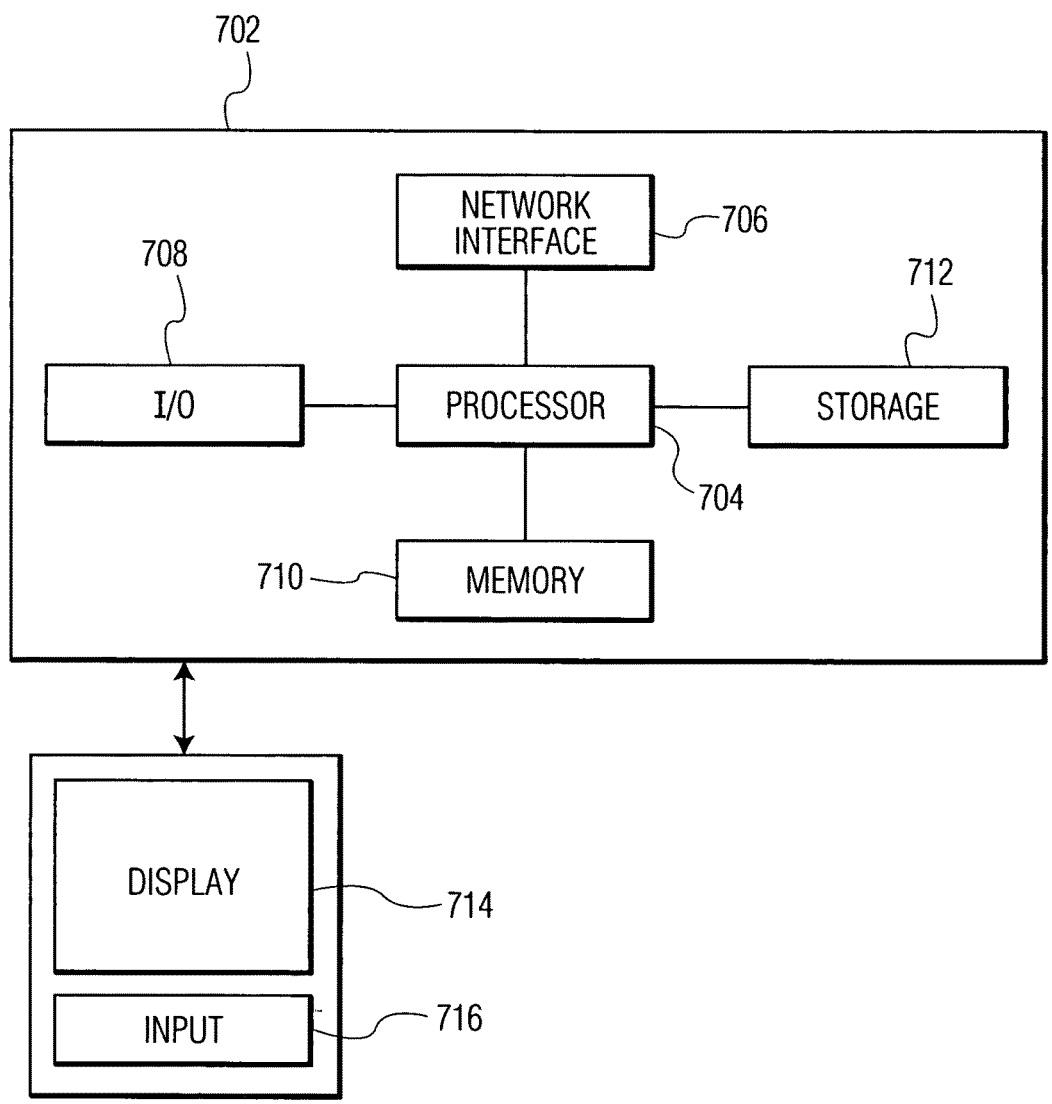
FIG. 7 illustrates a high level block diagram of a computer capable of implementing the present invention.

The method for enhanced viewing of rib metastasis in CT volume data and the rib metastasis visualization system can be implemented on a computer using well known computer processors, memory units, storage devices, computer software, and other components. A high level block diagram of such a computer is illustrated in FIG. 7. Computer 702 contains a processor 704 which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, applications to perform the steps of the above described method, such as automatically labeling the ribs and detecting alterations in the rib structure can be defined by the computer program instructions stored in the memory 710 and/or storage 712 and controlled by the processor 704 executing the computer program instructions. The computer 702 also includes one or more network interfaces 706 for communicating with other devices via a network. The computer 702 also includes a display 714 and a user input device 716. According to an embodiment of the present invention, the display 714 is controlled by the processor 704 to display the system interface 200 of FIG. 2. The user input device 716 is a device, such as a mouse, keyboard, etc., that allows users to interact with the system interface 200 displayed on the display 714. The computer 702 can also include additional input/output 708 which represents devices which allow for user interaction with the computer 702 (e.g., display, keyboard, mouse, speakers, buttons, etc.) One skilled in the art will recognize that an implementation of an actual computer will contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A computer implemented method for processing computed tomography (CT) volume data, comprising:
   receiving CT volume data;
   automatically segmenting a plurality ribs from said CT volume data; and
   automatically detecting alterations in said plurality of ribs by using shape-based analysis on each segmented rib to detect, for each segmented rib, intensity changes in trabecular bone or cortical bone and broken rib boundaries, and identifying a type of alteration for each detected alteration in each segmented rib.

2. The method of claim 1, further comprising:
   automatically ordering said plurality of ribs based on a size and shape of each rib; and
   automatically assigning a label to each of the ordered plurality of ribs based on a relative position of each rib.

3. The method of claim 2, wherein said step of ordering said plurality of ribs comprises:
   ordering said plurality of ribs based on relative spatial relationships and length ratios of said plurality of ribs.

4. The method of claim 2, further comprising:
   displaying at least one slice of said CT volume data.

5. The method of claim 4, further comprising:
   displaying the label assigned to at least one rib in said at least one slice of said CT volume data.

6. The method of claim 4, further comprising:
   generating a 3D visualization of said segmented plurality of ribs; and
   displaying said 3D visualization.

7. The method of claim 6, wherein said step of displaying at least one slice of said CT volume data comprises:
   displaying a slice corresponding to a user selection on said displayed 3D visualization; and
   marking on the displayed slice a location of said user selection on said 3D visualization.

8. The method of claim 6, further comprising:
   marking on at least one of said 3D visualization and said at least one slice locations of said alterations.

9. The method of claim 1, wherein said step of detecting alterations further comprises:
   filtering locations of alterations determined using the shape based analysis; and generating a visual indicator corresponding to each of the determined locations.

10. A non-transitory computer readable medium storing computer program instructions for performing a method for processing computed tomography (CT) volume data, the computer program instructions defining the steps comprising:
   automatically segmenting a plurality ribs from said CT volume data; and
   automatically detecting alterations in said plurality of ribs by using shape-based analysis on each segmented rib to detect, for each segmented rib, intensity changes in trabecular bone or cortical bone and broken rib boundaries, and identifying a type of alteration for each detected alteration in each segmented rib.

11. The computer readable medium of claim 10, further comprising computer program instructions defining the steps of:
   ordering said plurality of ribs based on a size and shape of each rib; and
   assigning a label to each of the ordered plurality of ribs based on a position a relative position of each rib.

12. The computer readable medium of claim 11, wherein the computer program instructions defining the step of ordering said plurality of ribs comprise computer program instructions defining the step of:
   ordering said plurality of ribs based on relative spatial relationships and length ratios of said plurality of ribs.

13. The computer readable medium of claim 11, further comprising computer program instructions defining the step of:
   displaying at least one slice of said CT volume data.

14. The computer readable medium of claim 13, further comprising computer program instructions defining the step of:
   displaying the label assigned to at least one rib in said at least one slice of said CT volume data.

15. The computer readable medium of claim 13, further comprising computer program instructions defining the step of:
   generating a 3D visualization of said segmented plurality of ribs; and
   displaying said 3D visualization.

16. The computer readable medium of claim 15, wherein the computer program instructions defining the step of displaying at least one slice of said CT volume data comprise computer program instructions defining the steps of:
   displaying a slice corresponding to a user selection on said displayed 3D visualization; and
   marking on the displayed slice a location of said user selection on said 3D visualization.

17. The computer readable medium of claim 15, further comprising computer program instructions defining the step of:
   marking on at least one of said 3D visualization and said at least one slice locations of said alterations.

18. The computer readable medium of claim 10, wherein the computer program instructions defining the step of detecting alterations further comprise computer program instructions defining the steps of:
   filtering locations of the alterations determined using the shape based analysis; and
   generating a visual indicator corresponding to each of the determined locations.

19. A system for processing computed tomography volume data comprising:
   a processor; and
   a memory to store computer program instructions, which when executed by the processor cause the processor to perform operations comprising:
   automatically segmenting a plurality ribs from said CT volume data; and
   automatically detecting alterations in said plurality of ribs by using shape-based analysis on each segmented rib to detect, for each segmented rib, intensity changes in trabecular bone or cortical bone and broken rib boundaries, and identifying a type of alteration for each detected alteration in each segmented rib.

20. The system of claim 19, wherein the operations further comprise:
   ordering said plurality of ribs based on a size and shape of each rib; and
   for assigning a label to each of the ordered plurality of ribs based on a position a relative position of each rib.

21. The system of claim 20, further comprising:
   a display configured to display at least one slice of said CT volume data, and configured to display a 3D visualization of said segmented plurality of ribs.

22. The system of claim 21, wherein the operations further comprise:
   means for marking locations of said alterations on at least one of said 3D visualization and said at least one slice locations of said alterations.

* * * * *